US00PP33590P2

(12) United States Plant Patent
Winslow

(10) Patent No.: US PP33,590 P2
(45) Date of Patent: Nov. 2, 2021

(54) OAK TREE NAMED 'MILLIKEN'

(50) Latin Name: *Quercus lyrata*
Varietal Denomination: Milliken

(71) Applicant: SELECT SPRING LLC, Hawkinsville, GA (US)

(72) Inventor: Stewart Peter Winslow, Drayton, SC (US)

(73) Assignee: SELECT SPRING LLC, Hawkinsville, GA (US)

( * ) Notice: Subject to any disclaimer, the term of this patent is extended or adjusted under 35 U.S.C. 154(b) by 0 days.

(21) Appl. No.: 16/953,288

(22) Filed: Nov. 19, 2020

(51) Int. Cl.
*A01H 5/00* (2018.01)
*A01H 6/00* (2018.01)

(52) U.S. Cl.
USPC ..... Plt./225

(58) Field of Classification Search
USPC ..... Plt./225
See application file for complete search history.

*Primary Examiner* — Susan McCormick Ewoldt
(74) *Attorney, Agent, or Firm* — C. Anne Whealy

(57) ABSTRACT

A new and distinct cultivar of Oak tree named 'Milliken', characterized by its upswept branching habit and columnar tree form; freely branching habit with numerous lateral branches providing a full and densely foliated appearance; and glossy dark green-colored leaves that become bright yellow in color in the autumn.

12 Drawing Sheets

Figure 1:
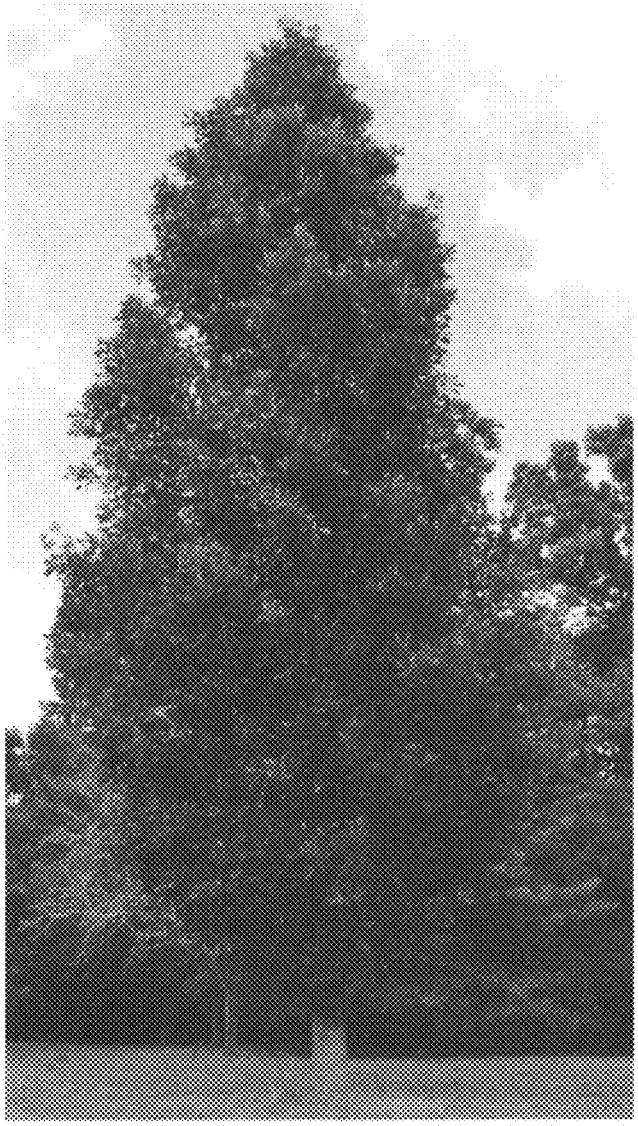

Botanical designation: *Quercus lyrata.*
Cultivar denomination: 'MILLIKEN'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of Oak tree, botanically known as *Quercus lyrata*, commercially referred to as Swamp Post Oak or Overcup Oak and hereinafter referred to by the name 'Milliken'.

The new Oak tree is a seedling from an open-pollination in 1995 of an unknown selection of *Quercus lyrata*, not patented, as the female, or seed, parent with an unknown selection of *Quercus lyrata* as the male, or pollen, parent. The new Oak tree was discovered and selected by the Inventor as a single plant from within the progeny of the stated open-pollination in a controlled environment in Spartanburg, S.C. in June, 1996.

Asexual reproduction of the new Oak tree by grafting in a controlled environment in Oconee County, Ga. since January, 2012 has shown that the unique features of this new Oak tree are stable and reproduced true to type in successive generations.

SUMMARY OF THE INVENTION

Trees of the new Oak have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Milliken'. These characteristics in combination distinguish 'Milliken' as a new and distinct Oak tree:

1. Upswept branching habit and columnar tree form.
2. Freely branching habit with numerous lateral branches providing a full and densely foliated appearance.
3. Glossy dark green-colored leaves that become bright yellow in color in the autumn.

Trees of the new Oak can be compared to trees of the female parent selection. Trees of the new Oak differ primarily from trees of the female parent selection in plant form as trees of the new Oak are columnar in shape with narrow branch angles whereas trees of the female parent selection are more broadly rounded in shape with wider branch angles.

Trees of the new Oak can also be compared to trees of *Quercus lyrata* 'Red Baron', not patented. In side-by-side comparisons, trees of the new Oak and 'Red Baron' differ primarily in the following characteristics:

1. Trees of the new Oak are columnar in shape with narrow branch angles whereas trees of 'Red Baron' are oval to rounded in shape with much wider branch angles.
2. Trees of the new Oak are narrower than trees of 'Red Baron'.
3. Leaves of trees of the new Oak and 'Red Baron' differ in fall leaf color as leaves of trees of the new Oak become bright yellow in color whereas leaves of trees of 'Red Baron' become reddish orange in color in the autumn.
4. Acorn cups of trees of the new Oak have a pebbly texture and cover about 70% of the fruit whereas acorn cups of trees of 'Red Baron' have a scaly texture and cover about 90% of the fruit.

BRIEF DESCRIPTION OF THE PHOTOGRAPHS

The accompanying colored photographs illustrate the overall appearance of the new Oak tree showing the colors as true as it is reasonably possible to obtain in colored reproductions of this type. Colors in the photographs may differ slightly from the color values cited in the detailed botanical description which accurately describe the colors of the new Oak tree grown in an outdoor nursery.

The photograph on the first sheet (FIG. 1) is a side perspective view of a typical mature tree of 'Milliken' grown during the summer.

Figure 2:
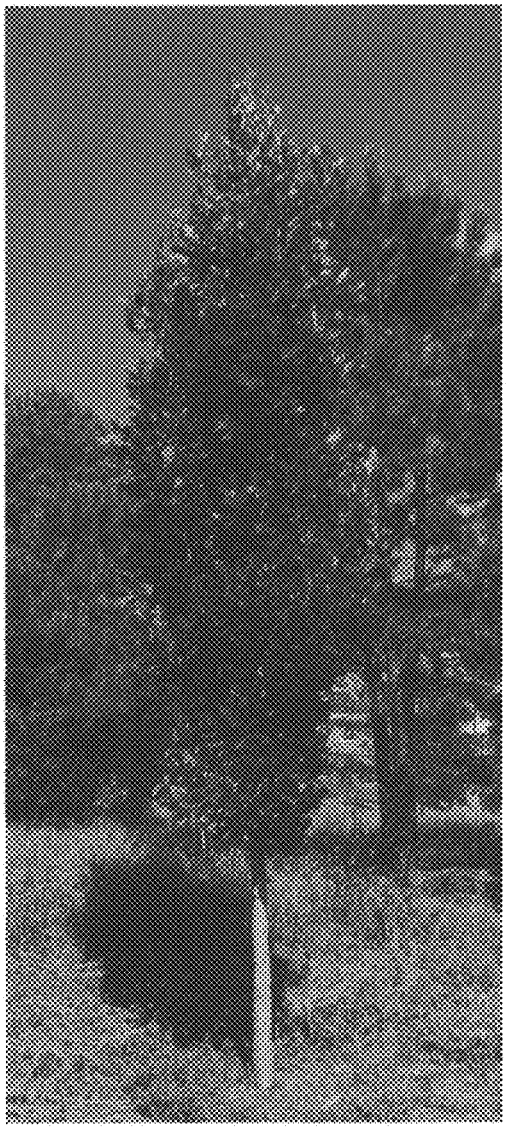

The photograph on the second sheet (FIG. 2) is a side perspective view of a grafted young tree of 'Milliken' grown during the summer.

Figure 3:
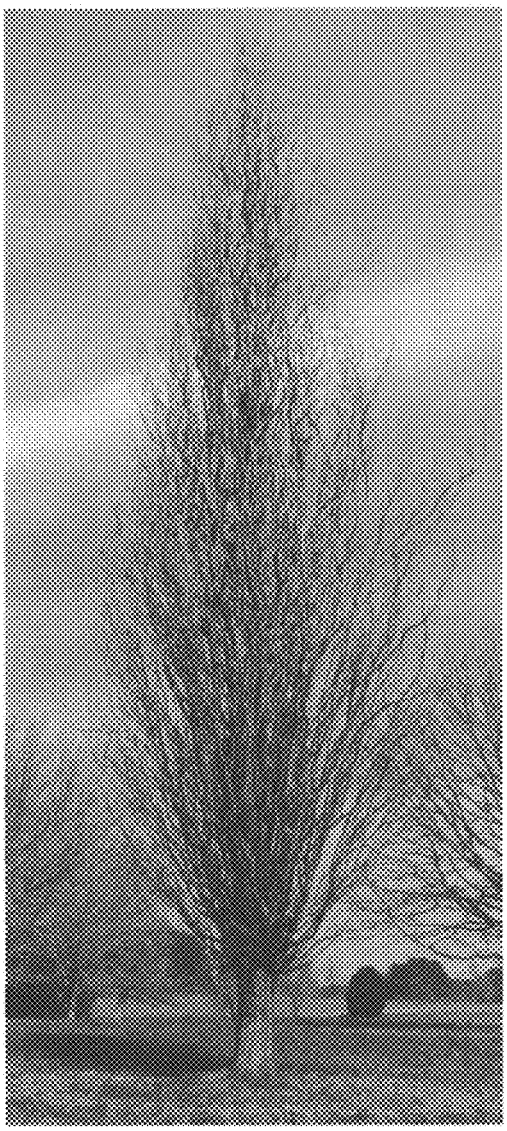

The photograph on the third sheet (FIG. 3) is a side perspective view of typical mature tree of 'Milliken' during the winter showing the upright and narrow branch angle.

Figure 4:
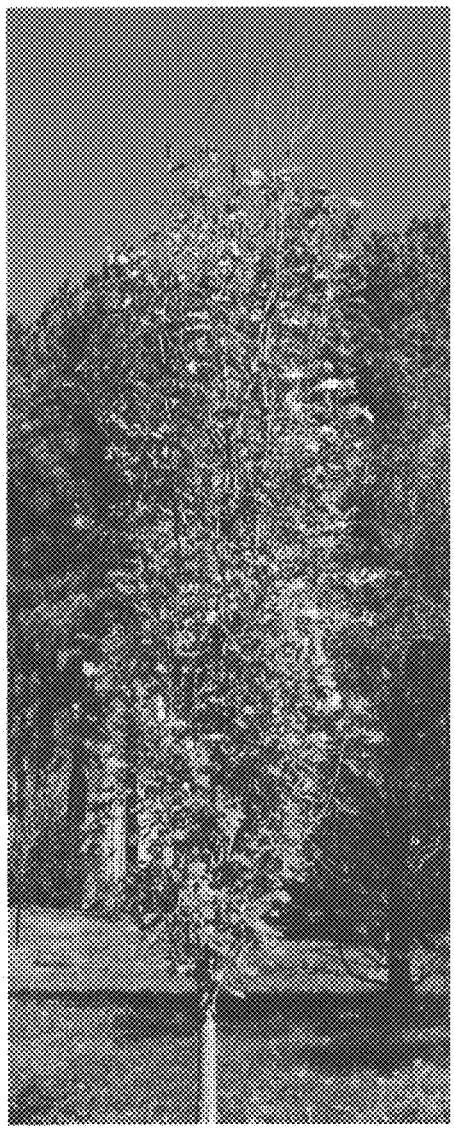

The photograph on the fourth sheet (FIG. 4) is a side perspective view of a grafted young tree of 'Milliken' grown during the autumn.

Figure 5:
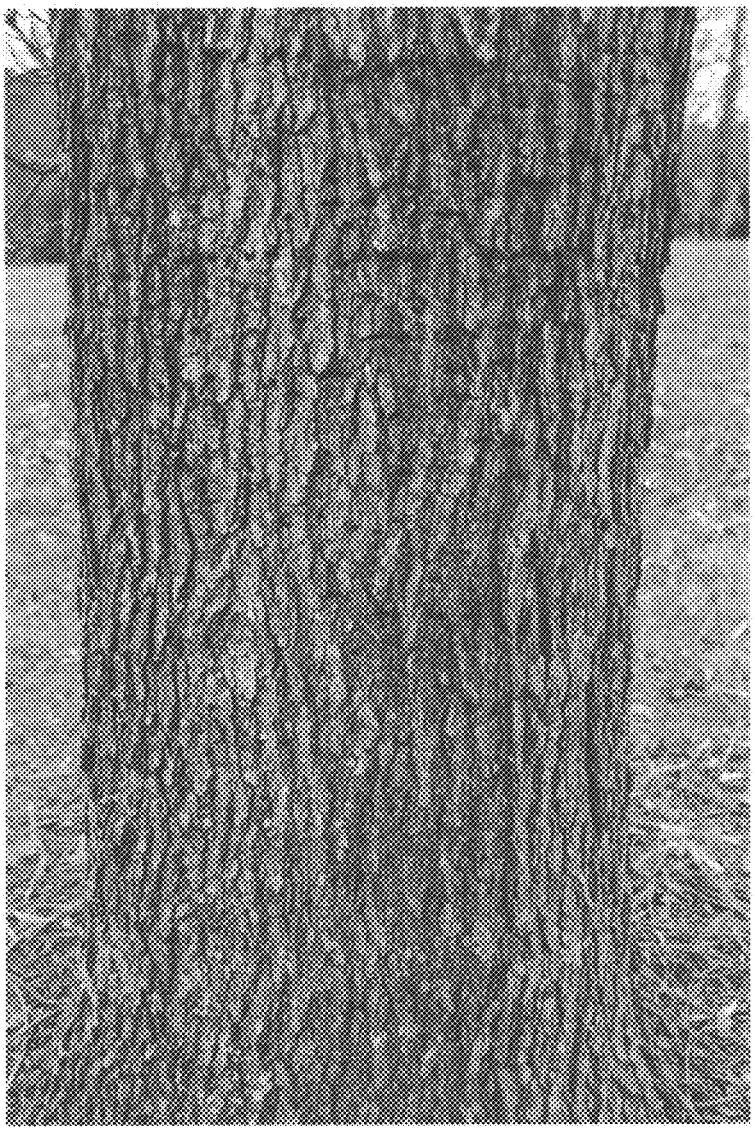

The photograph on the fifth sheet (FIG. 5) is a close-up view of the trunk of a typical mature tree of 'Milliken'.

Figure 6:
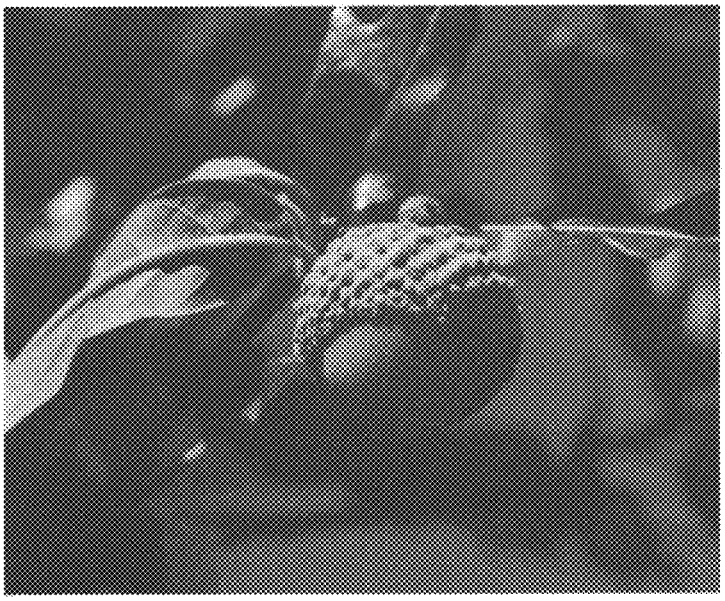

The photograph on the sixth sheet (FIG. 6) is a close-up view of a typical acorn of 'Milliken'.

Figure 7:
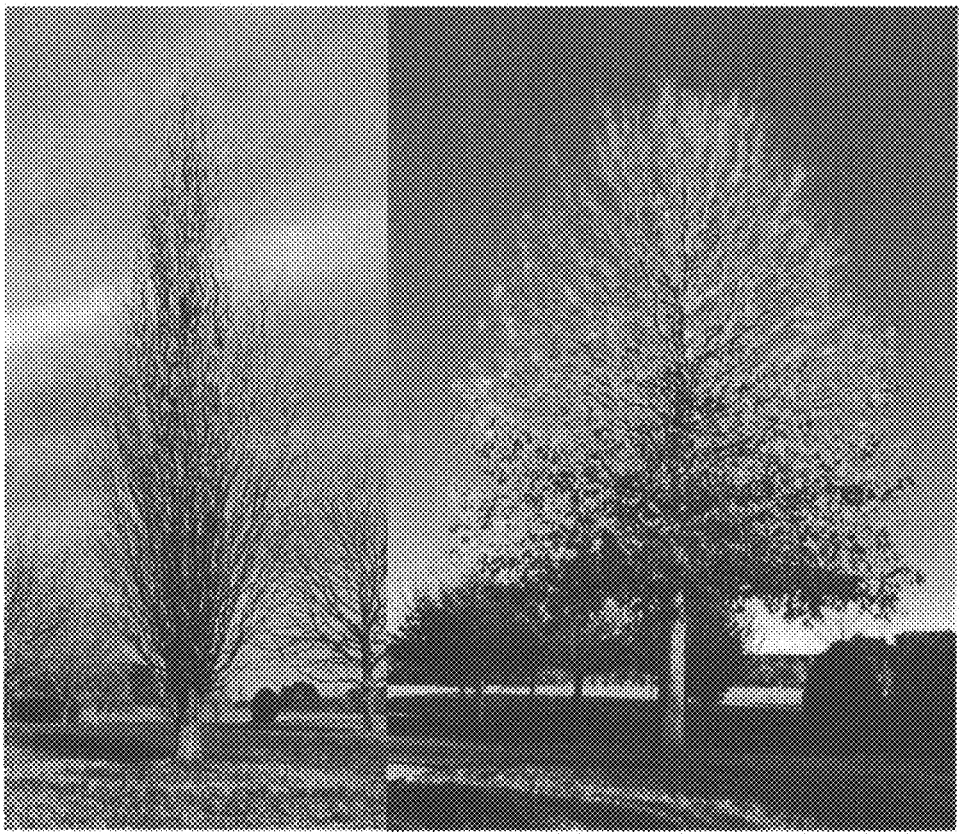

The photographs on the seventh sheet (FIG. 7) are side perspective views of typical trees of 'Milliken' (left) and 'Red Baron' (right) during the winter showing the differences in branch angle orientation.

Figure 8:
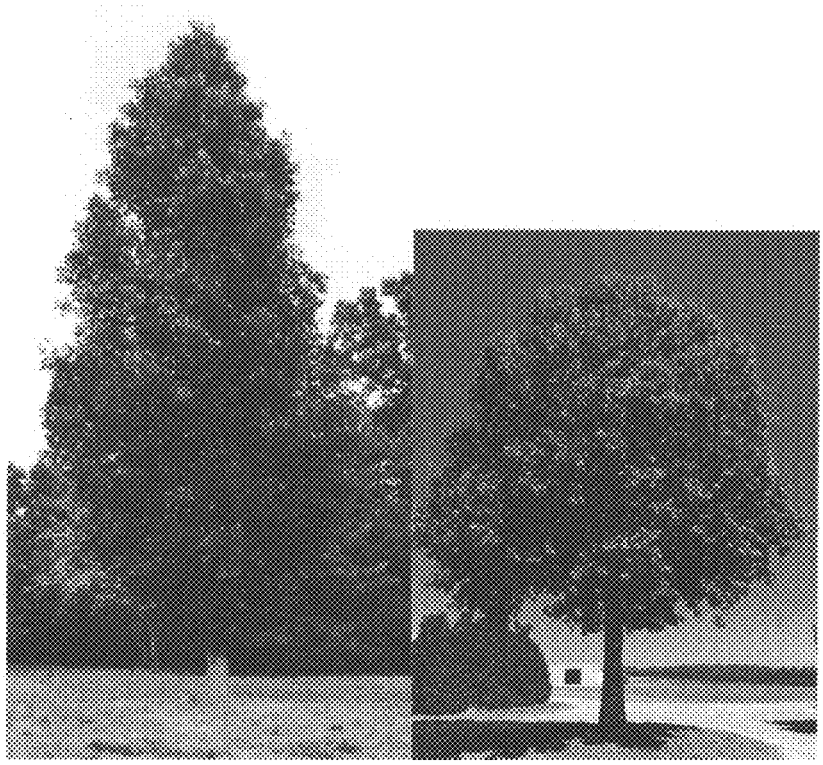

The photographs on the eighth sheet (FIG. 8) are side perspective views of typical trees of 'Milliken' (left) and 'Red Baron' (right) during the summer showing the differences in showing the differences in overall tree form.

Figure 9:
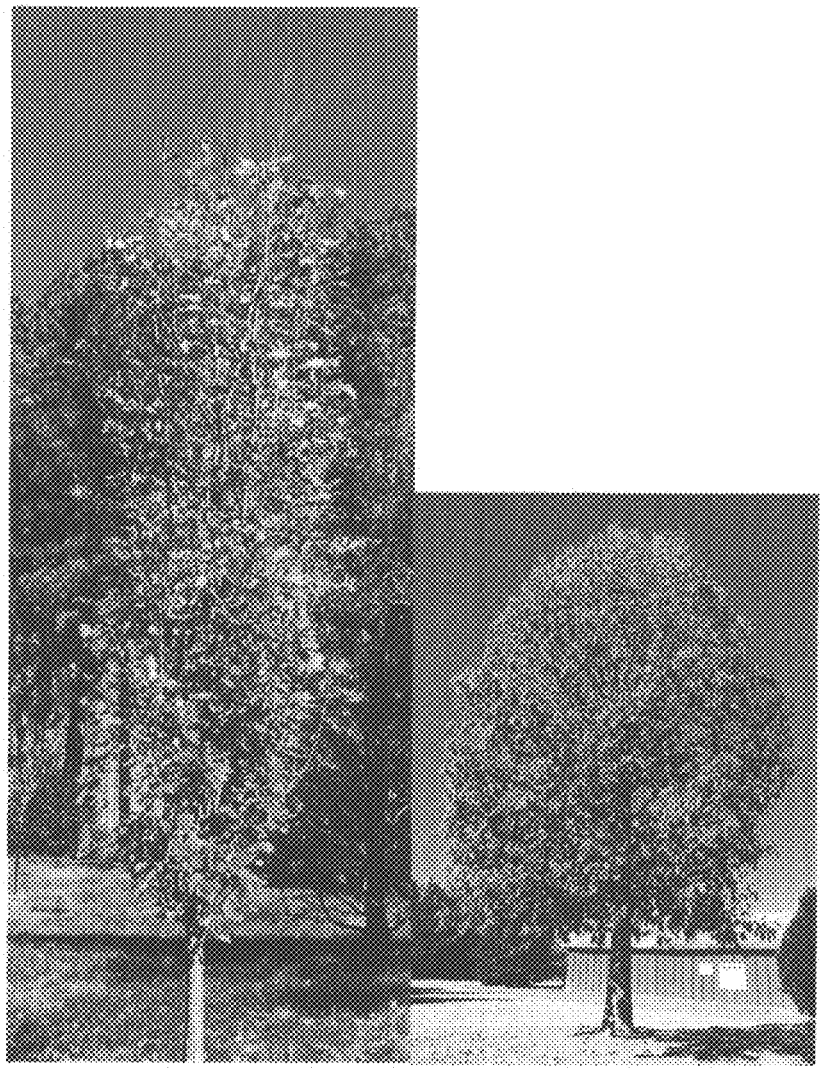

The photographs on the ninth sheet (FIG. 9) are side perspective views of typical trees of 'Milliken' (left) and 'Red Baron' (right) during the autumn showing the differences in fall leaf color.

Figure 10:
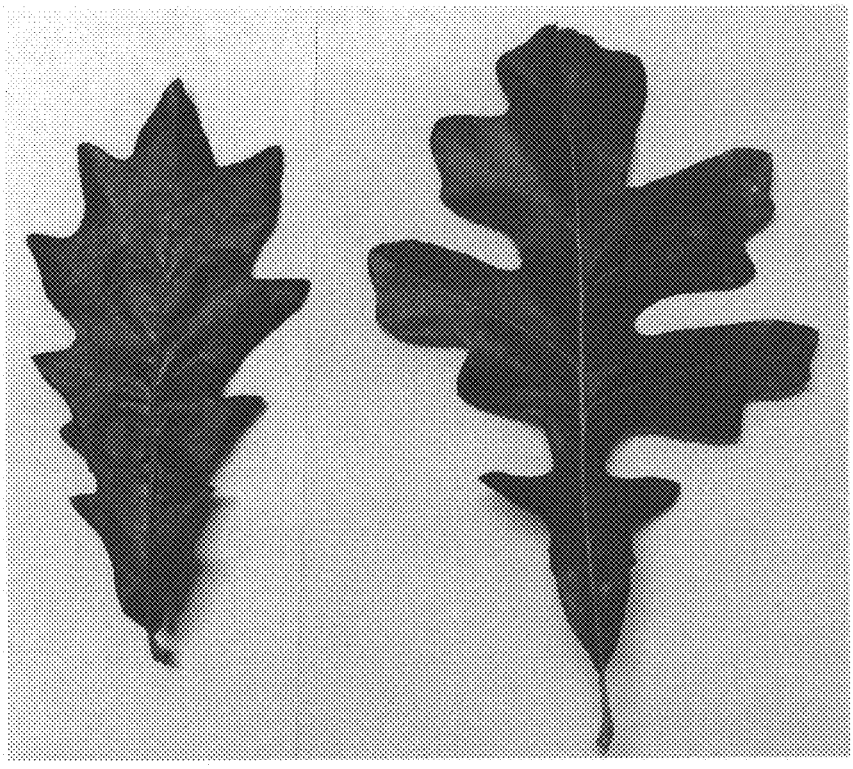

The photograph on the tenth sheet (FIG. 10) is a close-up view of the upper surfaces of typical leaves of 'Milliken' (left) and 'Red Baron' (right).

Figure 11:
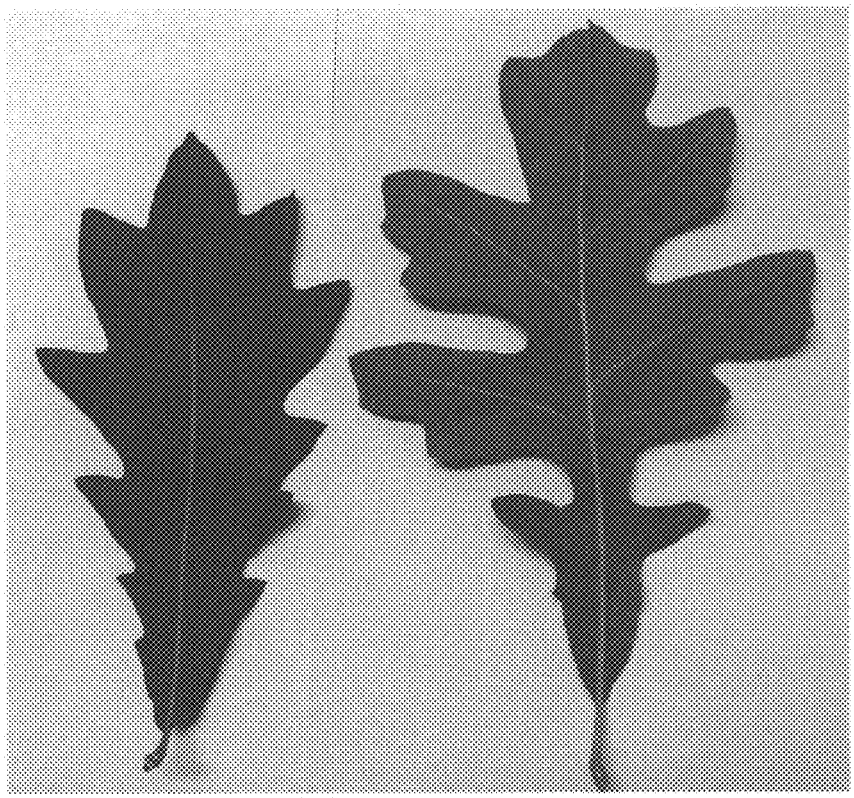

The photograph on the eleventh sheet (FIG. 11) is a close-up view of the lower surfaces of typical leaves of 'Milliken' (left) and 'Red Baron' (right).

Figure 12:
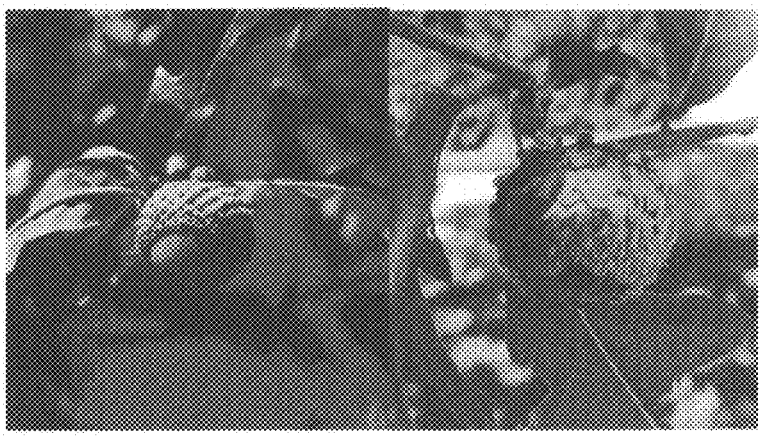

The photographs on the twelfth sheet (FIG. 12) are close-up views of typical acorns of 'Milliken' (left) and 'Red Baron' (right) showing the differences in texture and size of the acorn cup.

DETAILED BOTANICAL DESCRIPTION

The aforementioned photographs and following observations, measurements and values describe trees grown in an outdoor nursery in Spartanburg County, Ga. and under cultural practices typical of commercial Oak tree production. Mature trees used in the photographs and description were 25 years old; younger trees used in the photographs were eight years old; and trees of 'Red Baron' used in the photographs were 23 years old. During the production of the trees, average day temperatures were 22° C. and average night temperatures were 11° C. In the following description, color references are made to The Royal Horticultural Society Colour Chart, 2007 Edition, except where general terms of ordinary dictionary significance are used.

Botanical classification: *Quercus lyrata* 'Milliken'.

Parentage:

*Female, or seed, parent*.—Unnamed selection of *Quercus lyrata*, not patented.

*Male, or pollen, parent*.—Unknown selection of *Quercus lyrata*, not patented.

Propagation:

*Type*.—By softwood cuttings; plants of the new Oak tree can also be propagated by grafting scions of the new Oak tree onto an unnamed selection of *Quercus lyrata* rootstock.

*Time to initiate roots during the summer*.—About 30 days at temperatures about 27° C.

*Time to produce a rooted young plant during the summer*.—About 300 days at temperatures about 27° C.

*Root description*.—Medium in thickness, fleshy; typically creamy white in color, actual color of the roots is dependent on substrate composition, water quality, fertilizer type and formulation, substrate temperature and physiological age of roots.

*Rooting habit*.—Not freely branching; sparse.

Tree description:

*Tree form and growth habit*.—Deciduous tree with upswept branching habit and columnar tree form; freely branching habit with numerous lateral branches developing per tree; full and densely-foliated appearance; vigorous growth habit.

*Tree height*.—About 15 meters.

*Tree width* (*spread*).—About 4.5 meters.

*Growth rate, height*.—About 61 cm per year.

*Branch angle orientation*.—Narrowly upright, about 10° to 26° from vertical.

*Internode length*.—About 3.7 cm on one-year old wood.

*Immature bark color*.—Close to 199C; lenticels, close to 199C.

*Mature bark color*.—On one-year growth, close to between 197A and 198A.

*Immature bark texture*.—Smooth, glabrous.

*Mature bark texture*.—Rough, woody.

*Leaf arrangement*.—Alternate, simple.

*Leaf length*.—About 12.7 cm.

*Leaf width*.—About 6.8 cm.

*Leaf shape*.—Obovate.

*Leaf apex*.—Acute to obtuse.

*Leaf base*.—Narrowly truncate to cuneate.

*Leaf margins*.—Medium to shallowly five to six-lobed with medium to shallow rounded to acute sinuses.

*Leaf venation*.—Pinnate.

*Leaf texture, upper surface*.—Smooth, glabrous.

*Leaf texture, lower surface*.—Mostly smooth, glabrous; venation, pubescent.

*Leaf luster, upper surface*.—Glossy.

*Leaf luster, lower surface*.—Slightly glossy.

*Leaf color*.—When developing and fully developed, upper surface: Close to 137A; in the autumn, close to 13B. When developing and fully developed, lower surface: Close to 148B.

*Leaf petioles*.—Length: About 12.3 cm. Diameter: About 1.7 mm. Texture, upper and lower surfaces: Smooth, glabrous. Color, upper and lower surfaces: Close to 160B.

*Acorns*.—Height: About 2.5 cm. Diameter: About 1.9 cm. Cup coverage: Cup covers about 70% of the fruit. Cup texture: Pebbly.

Temperature tolerance: Trees of the new Oak have been observed to tolerate high temperatures about 40° C. and low temperatures about −15° C. and are suitable for USDA Hardiness Zones 5 to 9.

Pathogen & pest resistance: Trees of the new Oak have been observed to be resistant to Powdery Mildew (*Erysiphe trina*) and Oakworm (*Anisota senatoria*). Trees of the new Oak have not been observed to be resistant to other pathogens and pests common to Oak trees.

It is claimed:

1. A new and distinct Oak tree named 'Milliken' as illustrated and described.

* * * * *